United States Patent [19]

Stempel et al.

[11] Patent Number: 5,300,103
[45] Date of Patent: Apr. 5, 1994

[54] THERMAL BLANKET AND ABSORBENT INTERFACING PAD THEREFOR

[75] Inventors: Emil Stempel, Northbrook; Kenneth E. Riedel, Naperville, both of Ill.

[73] Assignee: Hollister Incorporated, Libertyville, Ill.

[21] Appl. No.: 950,391

[22] Filed: Sep. 24, 1992

[51] Int. Cl.⁵ .................................................. A61F 7/00
[52] U.S. Cl. .................................... 607/108; 607/112; 604/291
[58] Field of Search ............... 607/104, 108–112, 607/114; 604/289–291, 304, 307–308, 336

[56] References Cited

U.S. PATENT DOCUMENTS

| | | |
|---|---|---|
| 3,596,657 | 8/1971 | Eidus . |
| 3,678,933 | 7/1972 | Moore et al. . |
| 3,748,436 | 7/1973 | Cossaboom . |
| 3,867,939 | 2/1975 | Moore et al. . |
| 3,888,248 | 6/1975 | Moore et al. . |
| 4,114,620 | 9/1978 | Moore et al. . |
| 4,149,541 | 4/1979 | Gammons et al. . |
| 4,397,315 | 8/1983 | Patel . |
| 4,477,325 | 10/1984 | Osburn .................. 604/336 X |
| 4,517,972 | 5/1985 | Finch, Jr. . |
| 4,534,354 | 8/1985 | Bonner, Jr. et al. . |
| 4,556,055 | 12/1985 | Bonner, Jr. . |
| 4,628,932 | 12/1986 | Tampa . |
| 4,753,240 | 6/1988 | Sparks . |
| 4,951,665 | 8/1990 | Schneider . |
| 4,982,736 | 1/1991 | Schneider . |
| 5,178,139 | 1/1993 | Angelillo et al. ................. 607/114 |

Primary Examiner—Angela D. Sykes
Attorney, Agent, or Firm—Tilton, Fallon, Lungmus

[57] ABSTRACT

A thermal blanket particularly suitable for post-operative therapy and a thermally-conductive, fluid-absorbing interfacing pad for use therewith. The pad includes an intermediate or core layer of a pliant, liquid-absorbing, hydrocolloid-containing skin barrier material having both wet and dry tack, a thin backing layer on one side of the intermediate layer, and a porous, fluid-transmitting (and preferably fluid-absorbing) facing layer on the opposite side of the intermediate layer. One or more adhesive patches detachably secure the blanket and pad together, such patches being formed of a pressure-sensitive adhesive material preferably having greater affinity for the surface of the blanket than for the surface of the backing layer of the pad. In one embodiment, the pad's facing layer is provided with openings that expose areas of the adhesive intermediate layer for direct contact between the intermediate layer and a patient's skin.

21 Claims, 3 Drawing Sheets

THERMAL BLANKET AND ABSORBENT INTERFACING PAD THEREFOR

BACKGROUND AND SUMMARY

The therapeutic use of thermal blankets having walls of flexible polymeric material that are sealed together to define a labyrinth of passages for the circulation of heating or cooling fluid is well known. While such therapy may involve either heating or cooling portions of the body, it is the cooling mode that in recent years has received particular attention because of its effectiveness in post-operative treatment and in connection with physical therapy. In particular, cold therapy following soft tissue trauma has been shown to reduce pain, swelling, blood loss, inflammation and hematoma formation. During the rehabilitative process, cold therapy has been utilized effectively to diminish inflammation and patient discomfort.

It has been found that two factors bearing on the effectiveness of cryotherapy are the rate of cooling of the treatment site and the capability of maintaining a preselected and constant cold temperature. Variations in the rate of cooling and in maintaining a constant temperature may be due to the type and amount of gauze placed between the thermal blanket and the treatment site. Ideally, the interface between a thermal blanket and a treatment site should promote, or at least not retard, rapid cooling of the site to a selected treatment temperature which may then be maintained without substantial variation throughout the period of treatment.

It has also been found that variations may occur because of differences in the amounts of fluid exuding from a wound or treatment site and the capacity of the dressing material to absorb that fluid. Frequent changing of a dressing is often necessary, particularly during the early post-operative period, and it is therefore important that the dressing interface be non-adherent as well as non-linting and absorbent. Over the duration of treatment, a gauze pad or other dressing material is normally replaced numerous times whereas a single thermal blanket is commonly used and reused throughout the treatment period.

An important aspect of this invention lies in providing a disposable interfacing pad for a reusable thermal blanket that has significantly higher thermal conductivity than conventional gauze pads or dressings while, at the same time, providing substantial fluid absorbency. When used to cover an exuding wound, the interfacing pad of this invention demonstrates a capacity to absorb and retain a large volume of fluid, drawing it away from the wound while at the same time maintaining a moist environment and a non-adhering and non-linting contact surface for promoting wound healing. Such advantages are achieved by means of a relatively thin multi-layer pad which makes direct contact both with the wound and its surrounding skin areas and with the surface of the thermal blanket.

In one embodiment of the invention, the multi-layer pad is generally U-shaped in outline and may be easily folded or formed to surround an incision or wound site at knee or shoulder locations. It comprises at least three layers, namely, a porous, fluid-transmitting and preferably fluid-absorbing facing layer, a thin, flexible, fluid-impervious backing layer, and an intermediate or core layer composed of a hydrocolloid-containing skin barrier material having both wet and dry tack. The pad has essentially the same configuration as the thermal blanket with which it is used and has a surface area at least as large, and preferably larger than, the surface area of the blanket. Passages extend through the blanket for the circulation of cold (or hot) thermal fluid, and the wall of the blanket facing the pad provides a smooth surface for releasable adhesive attachment to the backing layer of the interfacing pad. Adhesive attachment means in the form of one or more pressure-sensitive adhesive patches releasably secure the blanket and pad together. Ideally, the patches are carried by the blanket and have substantially greater affinity for the polymeric material of the blanket wall than for the (material of the pad's backing layer, thereby promoting a clean separation of the adhesive from the backing layer when replacement of an interfacing pad is required.

In one embodiment of the invention, the porous, fluid-transmitting facing layer of the pad may be provided with apertures or openings through which surface portions of the hydrocolloid-containing intermediate layer are exposed. Such exposed portions of the adhesive intermediate layer may be brought into direct contact with skin surfaces about a wound or incision site for helping to hold the pad (and blanket) in a selected location and shaped condition.

Most advantageously, the intermediate or core layer of skin barrier material contains, in addition to at least one water-absorbing particulate hydrocolloid and a water-insoluble dry-tack-providing elastomer such as polyisobutylene, a copolymer resin capable of being cross linked when the composition is subjected to ionizing irradiation to form a cross-linked polymer network, as disclosed in co-owned U.S. Pat. No. 4,477,325, since such a skin barrier composition when used herein results in an interfacing pad capable of absorbing relatively large amounts of fluid without losing cohesive strength and disintegrating.

Other features, advantages, and objects of the invention will become apparent from the specification and drawings.

DETAILED DESCRIPTION OF PREFERRED EMBODIMENTS

Figure 3:
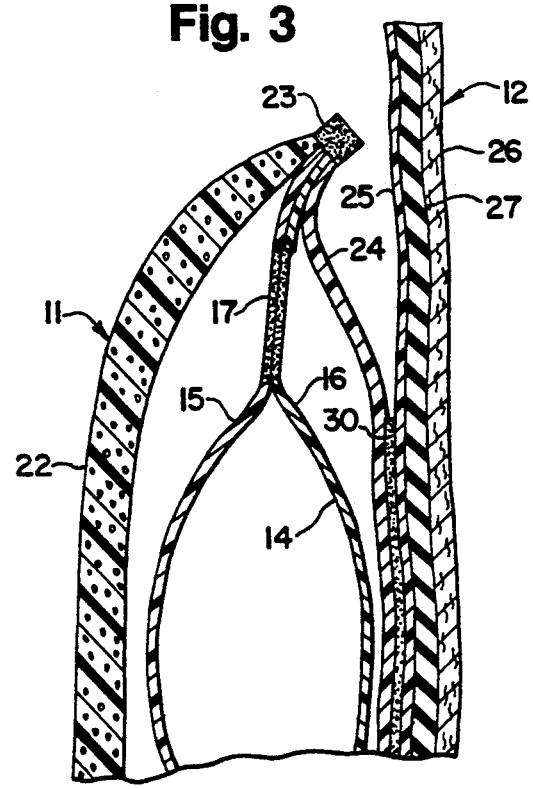
FIG. 3 is an enlarged fragmentary sectional view taken along line 3—3 of FIG. 2.

Referring to the drawings, the numeral 10 generally designates the combination of a thermal blanket 11 and an interfacing pad 12. Except as noted below, the thermal pad is of known construction, being similar to a blanket marketed by InCare Medical Products, Libertyville, Ill., under the designation HOT/ICE blanket. As shown in FIG. 3, the blanket 11 has flow passages 14 defined by thermoplastic sheets 15 and 16 sealed together along heat seal lines 17 to define a labyrinth of such passages for the circulation of hot or cold fluid. Flexible tubes 18 communicate with the passages 14 and hermaphroditic coupling elements 19 of the type disclosed in co-owned U.S. Pat. Nos. 4,951,665 and 4,982,736 connect the blanket to tubes 20 leading to equipment 21 of any suitable known type for heating, cooling, and pumping the thermal fluid through the system.

Blanket 11 preferably includes an outer wall 22 of soft, resilient, closed-cell, thermoplastic foam secured to flexible sheets 15 and 16 along peripheral heat seal zone 23. In the embodiment illustrated, the blanket is generally U-shaped in outline, a configuration found particularly useful in conforming the blanket to the contour of a patient's leg 13 around a site 13a of injury or surgery to the knee, and also for wrapping or shaping the blanket about a wearer's shoulder for cryotherapy following injury or surgery at that location.

The features of the thermal blanket so far described are known in the art. Unlike prior blankets, however, blanket 11 also has a thin, flexible patient-facing wall or panel 24 formed of a flexible polymeric material such as, for example, polyvinylchloride. Wall 24 is secured only at its periphery to sheets 15, 16, and 22, along heat seal zone 23, thereby providing a smooth, fluid impervious, flexible and conformable surface for contact with interfacing pad 12.

Figure 1:
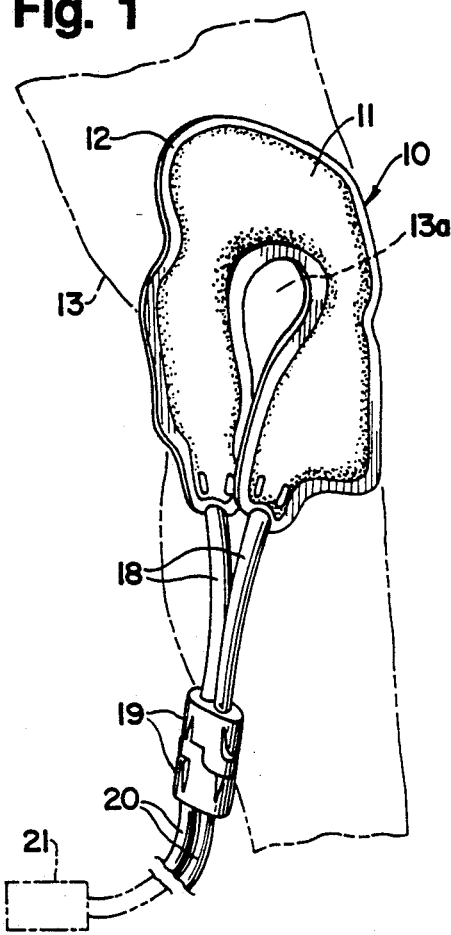
FIG. 1 is a perspective view illustrating the combination of a thermal blanket and interfacing pad as the elements would be positioned for cryotherapy following injury or surgery of the knee.
Figure 2:
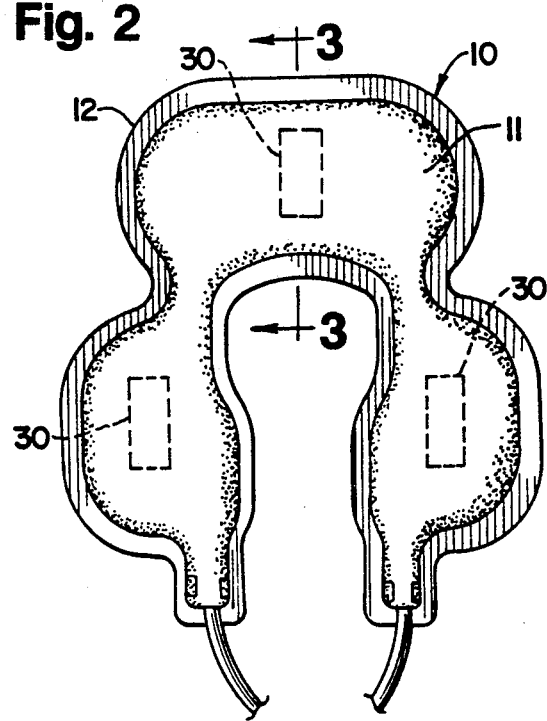
FIG. 2 is a plan view of the combination blanket/pad.

The interfacing pad 12 has generally the same outline as blanket 11 but with a surface area at least as large, and preferably somewhat larger than, that of blanket 11 (see FIGS. 1, 2). Pad 12 is multi-layered and comprises a backing layer 25, a patient-facing layer 26, and an intermediate layer 27. The pad is highly flexible and conformable, thermally conductive, and fluid absorbent. Intermediate layer 27 plays a major role with respect to absorbency, being composed of a soft, pliant, hydrocolloid-containing adhesive skin barrier material as used in the ostomy and wound care fields. The skin barrier composition includes an elastomer such as polyisobutylene which, together with the hydrocolloid or hydrocolloids dispersed therein, provides both wet and dry tack. Reference may be had to co-owned U.S. Pat. Nos. 4,477,325, 4,578,065, and 4,738,257 for skin barrier compositions that may be used for the fluid-absorbing intermediate layer 27. Since the material of the intermediate layer provides both wet and dry tack, the intermediate layer also constitutes the adhesive means for maintaining all three layers together.

The thickness of the intermediate layer 27 must be sufficient to insure adequate fluid absorbency without objectionably reducing thermal transmission. A thickness within the range of about 10 to 30 mil (0.25 to 0.76 mm) is believed to be suitable, with a thickness of about 20 ml (0.51 mm) being preferred. At that preferred thickness, the intermediate layer 27 of an interfacing knee pad having the configuration shown, combined with an absorbent facing layer 26, have the capability of absorbing and retaining at least 50 cc water over an interval corresponding with a typical three-day replacement period of such a pad in ordinary use. While the intermediate layer swells as it absorbs fluid, thereby increasing in thickness, any reduction in thermal conductivity resulting from the thickness increase is offset by the enhancement of conductivity produced by the increased moisture content.

It is important that as the intermediate layer absorbs fluid and swells, it continues to maintain its integrity and cohesive strength since a failure to do so would reduce the ability of the intermediate layer to function as a thermal transfer agent and would generally degrade the performance of the interfacing pad. Aforementioned U.S. Pat. No. 4,477,325 discloses a cross-linked barrier that is believed particularly effective for use as the composition of the intermediate layer 27. The cross-linked polymer network of ethylvinyl acetate resin, in combination with one or more hydrocolloids dispersed in polyisobutylene or other water-insoluble elastomer to provide the composition with both wet and dry tack, results in a composition which is resistant to degradation as it absorbs fluids. The cross-linking of such a mixture as disclosed in U.S. Pat. No. 4,477,325 is achieved by subjecting the mixture to ionizing gamma irradiation. Since such irradiation also effects sterilization, the result is a sterile intermediate or core layer and, if such irradiation is carried out after the layers of the pad have been assembled (a preferred procedure), then the result is a pad sterilized in its entirety with a core layer cross-linked by the same sterilizing irradiation.

The porous facing layer 26 must be thin, fluid-transmitting, non-linting, thermally conductive, at least in the presence of moisture, and should be non-adhering to a wound site. It is also preferably absorbent because, among other advantages, liquid absorbency or retention is believed to enhance thermal conductivity. An absorbent, non-woven synthetic fabric, such as the polyester/rayon blend of spunlaced fabric available under the designation Sontara 8423 from E. I. du pont de Nemours, Wilmington, Del., has been found particularly effective but other soft, porous materials having similar properties may be used. The facing layer need not be composed of fabric; a hydrophilic open-cell foam such as the polyurethane foam marketed under the designation Acquell by Scotfoam Corporation, Eddystone, Pa., may also be used. In any event, the thickness of the facing layer 26, like of the intermediate layer 27, should not compromise the thermal conductivity of the pad. In general, the thickness of the facing layer 26 should fall within the range of about 5 to 30 ml (0.12 to 0.76 mm) with the preferred range being about 10 to 15 mil (0.25 to 0.38 mm) as measured by means of a standard caliper-type thickness gage.

In a preferred embodiment, the facing layer serves both as an absorbent layer and as a conduit for the migration of fluids from the patient's skin or wound to the absorbent intermediate layer 27. The effect in use is that the facing layer 26 is moistened by fluids at the wound site but, before the facing layer can become saturated, fluids travel through the pores and are absorbed by the hydrocolloid-containing intermediate layer 27. The pad therefore maintains a moist interface between the thermal blanket and the wound site that promotes wound healing while at the same time drawing off excess fluids and retaining them out of direct contact with the wound.

Backing layer 25 should be tough, smooth, flexible, and fluid-impermeable. A thin metallic foil or metalized film may be used, but it has been found that if the backing layer is thin enough, generally within the range of 1 to 3 mil 0.03 to 0.07 mm), the use of a non-metallic polymeric film will not have a significant adverse effect on thermal conductivity. A polymethylpentene film having a thickness of about 2 mil is preferred, but other polymeric films formed of materials such as polyester, polyurethane, ethylene-vinyl acetate copolymer, polyvinylidene fluoride, or low density polyethylene, may also be used. All of such materials are capable of adhering to pressure-sensitive adhesive attachment means carried by the thermal blanket 11 while at the same time having good release properties that insure a clean release from such attachment means when replacement of an interfacing pad is desired.

Figure 4:
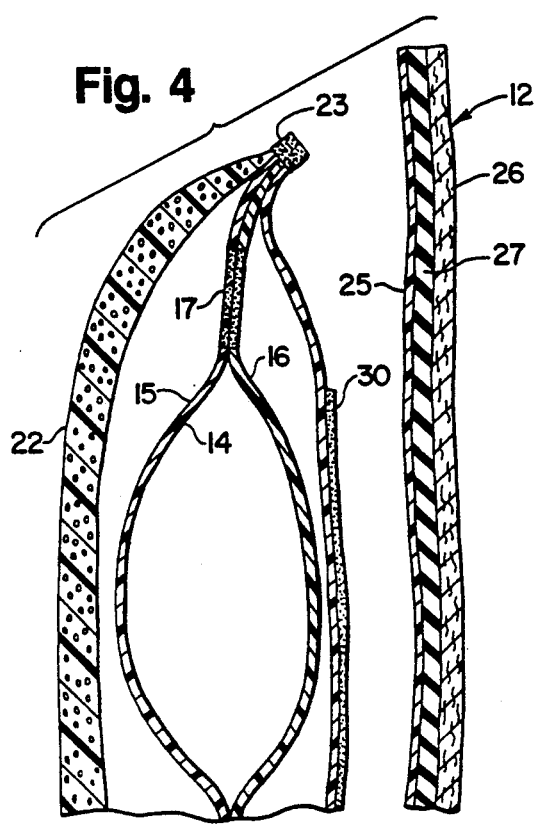
FIG. 4 is a sectional view similar to FIG. 3 but depicting the elements of the combination in separated condition.

The adhesive attachment means shown in FIGS. 2 and 4 takes the form of a plurality of patches 30 affixed to the outer surface of blanket wall 24. The patches may be transferred, coated, or otherwise applied to wall 24 and should be composed of a pressure-sensitive adhesive that has greater affinity for the material of blanket wall 24 (commonly PVC) than for the backing film 25 of interfacing pad 12. Thus, when replacement of an interfacing pad is required, the pad will separate cleanly from the adhesive patches 30 which then remain with the thermal blanket 11 to provide the attachment means for a replacement pad 12.

Any of a variety of pressure-sensitive adhesives having good adhesion to the flexible PVC (or other polymer) of the thermal blanket may be used. One such adhesive is acrylic transfer tape adhesive F-9465 PC marketed by 3M HealthCare, St. Paul, Minn. Such adhesive is particularly suitable because it is capable of fully releasing from the backing layer of the interfacing pad, adheres securely to the patient-facing wall or panel of the blanket, and resists plasticizer migration from the films which it contacts.

Figure 6:
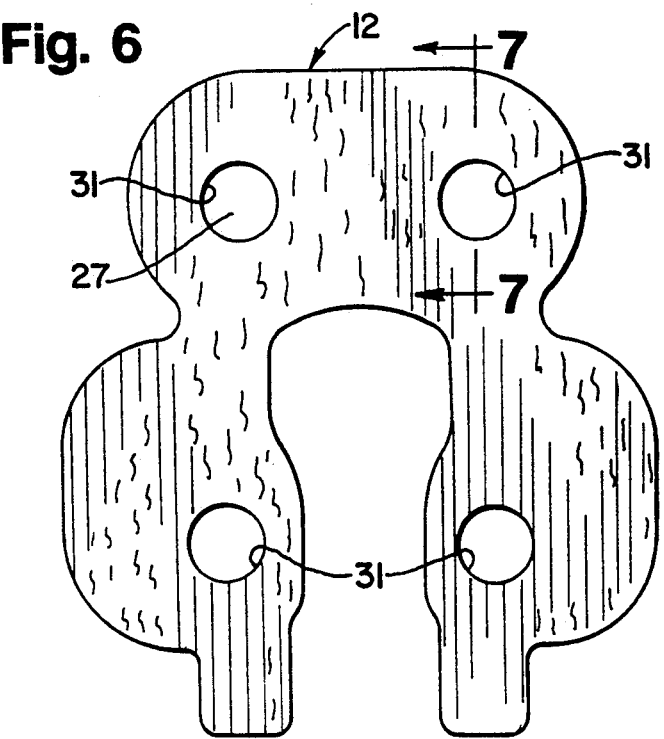
FIG. 6 is a plan view from the underside of a thermal blanket constituting a second embodiment of this invention.
Figure 7:
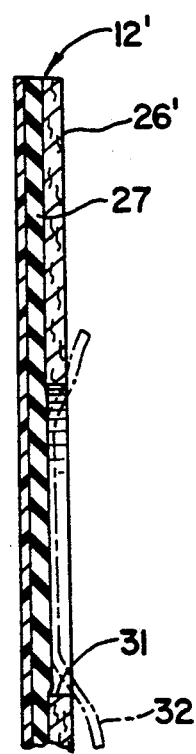
FIG. 7 is a fragmentary enlarged sectional view taken along line 7—7 of FIG. 6.

While both the intermediate layer 27 and the facing layer 26 of the pad 12 are shown to be continuous, in some cases it may be desirable to provide one or both with suitable openings or interruptions. For example, the intermediate layer may be provided with a multiplicity of openings that serve as fluid-retention reservoirs or may even take the form of parallel strips of barrier material interposed between the facing and backing layers. FIGS. 6 and 7 depict an alternate embodiment in which pad 12' is identical to the pad already described except that facing layer 26' is provided with a plurality of openings 31 which expose the intermediate layer 27 therethrough. Since the intermediate layer is formed of barrier material having both wet and dry tack, the portions of intermediate layer 27 exposed through the openings 31 provide tacking means for locating and at least temporarily securing the pad against a patient's skin in an area surrounding the surgical site. It is to be understood that the openings 31 would be covered by suitable release sheets 32 (FIG. 7) that would be removed by the user at the time of application.

Figure 5:
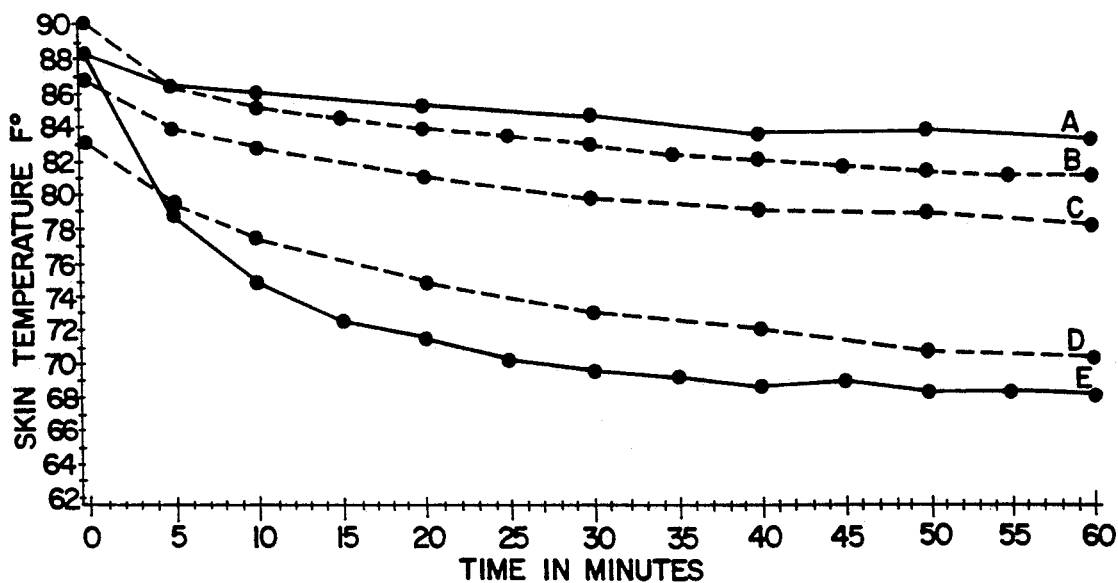
FIG. 5 is a graph comparing the cooling effectiveness of a thermal blanket used with an interfacing pad of this invention and with conventional gauze dressings.

FIG. 5 depicts the results of a comparison study using a thermal blanket of a preferred embodiment as disclosed herein with (A) a skin covering of two layers of dry gauze, (B) two layers of wet gauze, (C) one layer of dry gauze, and interfacing pads 12 as disclosed herein (D) in dry condition and (E) in wet condition. Both the wet interfacing pad (E) and the wet gauze (B) were sprayed with 10 cc of water along an imaginary suture line prior to applying the pad or gauze to the skin. The coolant solution circulating through the thermal blanket was pre-set to 50 degrees F. and maintained at that temperature for all subjects. The graph reveals that within 20 minutes from initiation of the cooling process, the skin temperature in contact with the wet interfacing pad (E) dropped to 71 degrees while the skin with the gauze wraps was still at 81 degrees (C), 84 degrees (B) or 85 degrees (A). Even when applied in a dry state, the interfacing pad (D) was far superior when used with thermal blanket 11 than any of the gauze wrappings (A) (B) (C), whether used wet or dry.

While in the foregoing we have disclosed embodiments of this invention in considerable detail for purposes of illustration, it will be understood by those skilled in the art that many of these details may be varied without departing from the spirit and scope of the invention.

We claim:

1. In combination, a flexible thermal blanket for therapeutic hot/cold treatment of a patient; said blanket having flow passages therethrough for the circulation of heated or cooled liquid and having a patient-facing wall of smooth, flexible, polymeric material; and an interfacing pad having a backing layer, a porous absorbent liquid-transmitting patient-facing layer, and an intermediate layer between said backing layer and said patient-facing layer of said pad of an adhesive hydrocolloid-containing liquid-absorbing skin barrier composition with both wet and dry tack; all of said layers being highly flexible and being secured together, said layers providing a body-conformable pad having an outline generally corresponding with that of said blanket and a surface area no smaller than that of said blanket; and adhesive attachment means releasably securing said backing layer of said pad to said patient-facing wall of said blanket.

2. The combination of claim 1 in which said patient-facing layer of said pad is also liquid-absorbing.

3. The combination of claim 2 in which said absorbent, porous, patient-facing layer is composed of a non-linting non-woven fabric.

4. The combination of claim 2 in which said absorbent, porous, facing layer is composed of hydrophilic open-cell polymeric foam.

5. The combination of claim 1 in which said interfacing pad is larger in area than said blanket.

6. The combination of claim 1 in which said layers of said pad are adhesively secured together by said intermediate layer.

7. The combination of claim 6 in which said absorbent patient-facing layer has a plurality of apertures exposing areas of said intermediate layer therethrough for direct limited adhesive contact of said intermediate layer with the skin of a patient.

8. The combination of claim 1 in which said skin barrier composition includes said hydrocolloid dispersed in a water-insoluble elastomer having dry tack and retained in a cross-linked polymer network.

9. The combination of claim 1 in which said blanket and pad are each generally U-shaped in outline.

10. The combination of claim 1 in which said adhesive attachment means comprises a plurality of patches of pressure-sensitive adhesive interposed between said backing layer and said patient-facing wall of said blanket.

11. The combination of claim 10 in which said patches are composed of an adhesive having greater affinity for said patient-facing wall of said blanket than for said backing layer so that said patches separate cleanly from said backing layer when said pad and blanket are separated.

12. The combination of claim 11 in which said patient-facing wall of said blanket is formed of polyvinylchloride, said backing layer of said interfacing pad is formed of polymethylpentene, and said patches are formed of an acrylic pressure-sensitive adhesive.

13. A multilayer interfacing pad for use as an absorbent, heat-transferring liner beneath a thermal blanket used for heating or cooling a body surface; said pad having a polymeric, liquid-impervious backing layer, a porous absorbent liquid-transmitting skin-contacting layer, and an intermediate layer therebetween of a hydrocolloid-containing liquid-absorbing skin barrier composition having both wet and dry tack.

14. The pad of claim 13 in which said skin-contacting layer of said pad is also liquid-absorbing.

15. The pad of claim 14 in which said absorbent, porous, skin-contacting layer is formed of a non-woven material of synthetic fibers.

16. The pad of claim 13 in which said skin barrier composition includes said hydrocolloid dispersed in a water-insoluble elastomer having dry tack and retained in a cross-linked polymer network.

17. The pad of claim 13 in which said layers of said pad are adhesively secured together by said intermediate layer.

18. The pad of claim 17 in which said absorbent skin-contacting layer has a plurality of apertures exposing areas of said intermediate layer therethrough for making limited adhesive contact with the skin of a patient.

19. The pad of claim 13 in which said pad is generally U-shaped in outline.

20. The pad of claim 13 in which said backing layer is formed of polymethylpentene.

21. The pad of claim 13 in which said backing layer has a thickness within the range of about 1 to 3 mil, said intermediate layer has a thickness within the range of about 10 to 30 mil, and said, skin-contacting layer has a thickness within the range of about 5 to 30 mil.

* * * * *